United States Patent
Fitzgerald et al.

(10) Patent No.: US 6,308,751 B1
(45) Date of Patent: Oct. 30, 2001

(54) LIQUID DISPENSING APPARATUS

(75) Inventors: Stephen Peter Fitzgerald; John Victor Lamont, both of Co. Antrim; Robert Ivan McConnell, Antrim; James Rudolf Meyer, Co. Antrim, all of (GB)

(73) Assignee: Randox Laboratories LTD, Antrim (GB)

( * ) Notice: Subject to any disclaimer, the term of this patent is extended or adjusted under 35 U.S.C. 154(b) by 0 days.

(21) Appl. No.: 09/552,751

(22) Filed: Apr. 19, 2000

(30) Foreign Application Priority Data

Jun. 4, 1999 (EP) .................................................. 99304366

(51) Int. Cl.$^7$ ...................................................... B65B 1/04
(52) U.S. Cl. ........................... 141/270; 141/130; 422/99; 422/100
(58) Field of Search ..................................... 141/130, 270, 141/284, 250; 422/99, 100, 104; 436/807, 47

(56) References Cited

U.S. PATENT DOCUMENTS

| 4,325,909 | * | 4/1982 | Coulter et al. .......................... 422/63 |
| 4,447,395 | | 5/1984 | Englar et al. . |
| 4,774,055 | * | 9/1988 | Wakatake et al. ...................... 422/64 |
| 5,645,800 | | 7/1997 | Masterson et al. . |

FOREIGN PATENT DOCUMENTS

| 0 692 717 A2 | 1/1996 | (EP) . |
| WO 93/21534 A1 | 10/1993 | (WO) . |

* cited by examiner

Primary Examiner—Steven O. Douglas
(74) Attorney, Agent, or Firm—Oliff & Berridge, PLC

(57) ABSTRACT

Liquid dispensing apparatus comprises a support member which supports a movably mounted dispensing member. The support member is movable between first and second positions. A single drive system causes the dispensing member to move relative to the support member to a number of dispense positions while the support member is in its first position and causes the support member to move to the second position.

11 Claims, 5 Drawing Sheets

LIQUID DISPENSING APPARATUS

FIELD OF THE INVENTION

The invention relates to liquid dispensing apparatus and is particularly concerned with apparatus for dispensing liquids in an assay device processing instrument.

DESCRIPTION OF THE PRIOR ART

There is a continuing need to automate assay device processing and various instruments have been devised for dealing with this. We describe an example of such an instrument in our co-pending European Patent Application No. 98307706.6. Typically, such an instrument comprises a number of modules for carrying out certain dedicated tasks and a well containing a material to be assayed is transported to each module in turn. We have found that there is a need to increase the speed of operation of liquid dispensing modules and, in particular, a signal reagent dispenser. By speeding up operation of such a dispenser, more time is permitted for other dispensers such as a main reagent dispenser to operate.

SUMMARY OF THE INVENTION

In accordance with the present invention, liquid dispensing apparatus comprises a support member which supports a movably mounted dispensing member, the support member being movable between a first position and at least one second position; and a single drive system for causing the dispensing member to move relative to the support member to a number of dispense positions while the support member is in its first position and for causing the support member to move to the or each second position.

We have devised a new type of apparatus which can automatically cause a dispensing member such as a dispensing tube or probe to pass each of a number of dispense positions and, typically thereafter, to cause the support member to move to one (or in some embodiments more) second positions which could be a wash station, a further dispense position, or a sample pick-up position, for example for diluent or a buffer.

In a preferred example, the drive system causes the dispensing member sequentially to move relative to the support member to the number of dispense positions while the support member is in its first position and thereafter causes the support member to move to the or each second position. However, the reverse operation could also occur with the support member initially in the or one of its second positions and then being driven by the drive system to the first position and thereafter the dispensing member being caused to move relative to the support member to the dispense positions.

The apparatus has a particularly simple form with a minimum of components and in particular a single drive system so that a single operation of the drive system causes the full sequential movement to occur. It is then only necessary to time the delivery of a liquid to coincide with the position of the dispensing member at each dispense position. This leads to a very rapid operation and a simple instrument which reduces the risk of breakdown.

The support member could move in a linear fashion between the first and second positions, for example by being slidably mounted to a base. Preferably, however, the support member is pivoted to a base for rotational movement between the first and second positions. This leads to a very simple mechanical arrangement in which the drive system may include a rotationally mounted drive member which rotates upon actuation of the drive system from first to second positions, during which the dispensing member moves to each of the dispense positions, and thereafter to one or more third positions while engaging the support member so as to rotate the support member to corresponding second positions.

Conveniently, the drive member is a pin supported on a rotatably mounted drive pinion. Other arrangements are also possible such as a clutch which is engaged when the drive member reaches a predetermined position.

Preferably, the support member is urged towards its first position, for example by a spring, although in other examples, the support member could be driven back to its first position upon reverse operation of the drive system.

Typically, the drive system includes a drive belt linking a drive motor of the drive system and the dispensing member. However, a drive gear arrangement could be used instead.

Preferably, the dispensing member is rotatably mounted to the support member although it could be slidably mounted in some cases. In the case of a rotatable mounting, the dispensing member preferably includes a carrier rotatably mounted to the support member, and a dispensing tube mounted to the carrier. The location of the dispensing tube on the carrier will depend upon the path which the tube must follow in order to reach the dispense positions and it is envisaged that a number of dispensing tube locations could be provided on the carrier so as to accommodate a variety of dispense position configurations.

As explained above, the apparatus has particular application to the dispensing of signal reagents in an automatic assay processing instrument. However, the apparatus could be used in other applications for dispensing other liquids.

BRIEF DESCRIPTION OF THE DRAWINGS

An example of a signal reagent dispenser according to the invention will now be described with reference to the accompanying drawings, in which.

DETAILED DESCRIPTION OF THE EMBODIMENT

Figure 1:
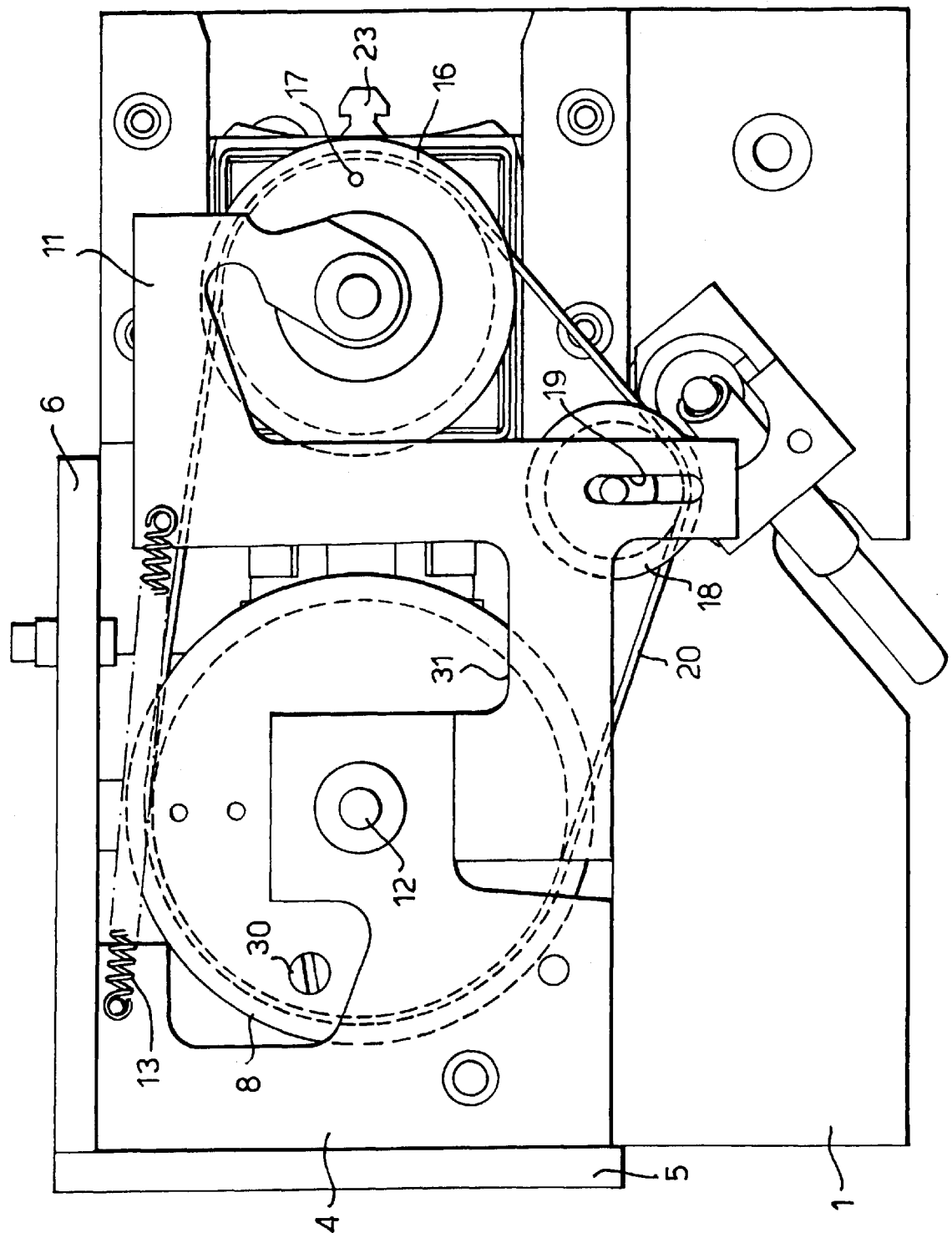
FIG. 1 is a plan of the dispenser with the support arm in its first or dispense position.
Figure 2:
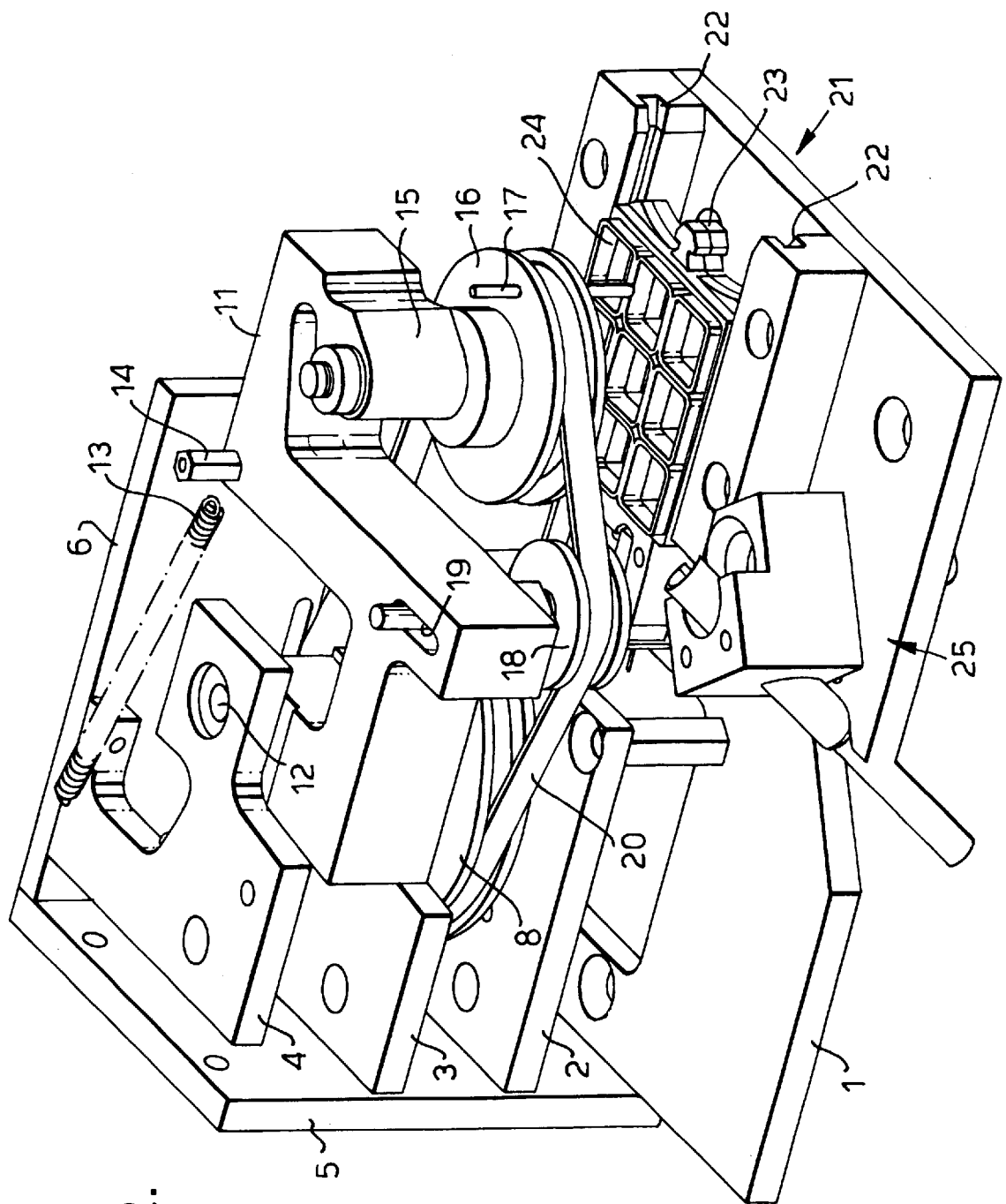
FIG. 2 is a perspective view of the dispenser in the position shown in FIG. 1 but with the motor omitted.
Figure 3:
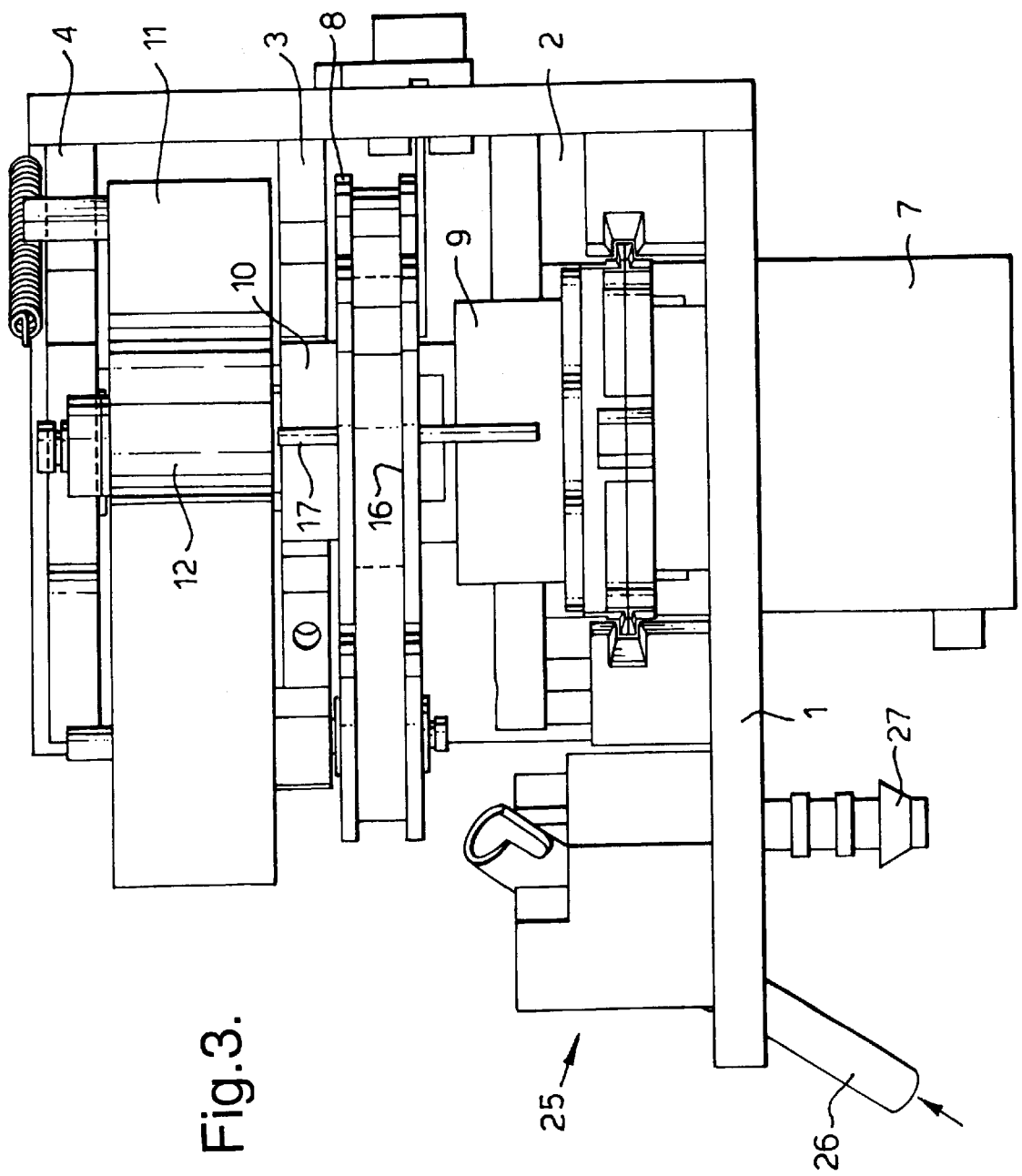
FIG. 3 is a side view of the dispenser in the position shown in FIG. 1.
Figure 4:
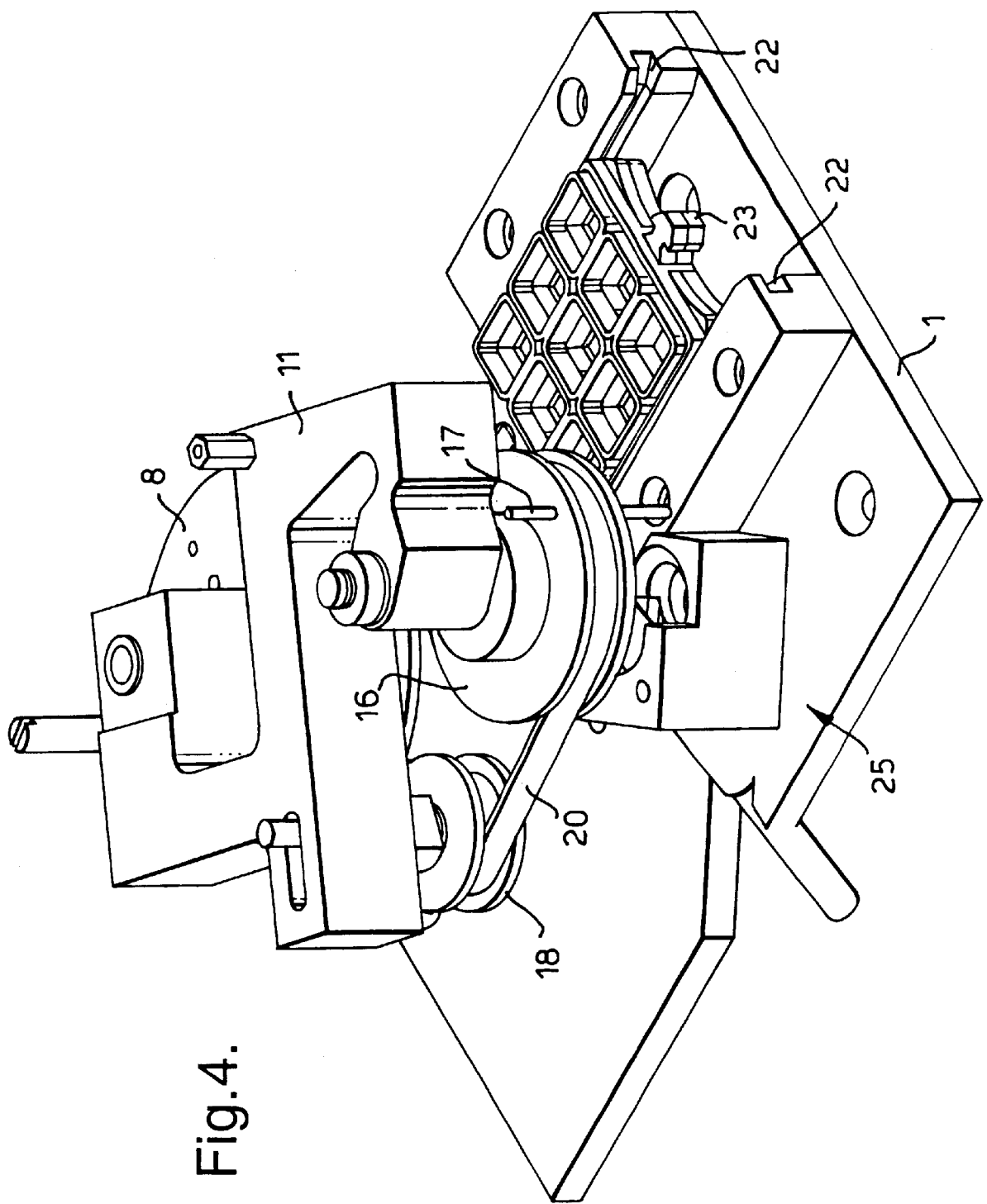
FIG. 4 is a perspective view of the dispenser with the support arm moved towards its second position.

As shown in FIGS. 1 to 3, the dispenser comprises a base 1 having a number of laterally extending plate supports 2–4 secured vertically spaced apart to a pair of side walls 5,6. A motor 7 is secured beneath the base 1 and will typically comprise a stepper motor. A drive pulley 8 is journalled in bearings 9,10 in the support plates 2,3 respectively and is driven by the motor 7 via a connection which is not visible in the drawings.

A support arm 11 is journalled in bearings between the support plates 3,4, the axis of rotation of the support arm being indicated at 12. As can be seen, this axis is coaxial with the axis of rotation of the drive pulley 8. The support arm 11 is urged towards the position (first or dispense) shown in FIGS. 1–3 by a tension spring 13 connected between the support plate 4 and a protrusion 14 on the support arm.

The spring is shown disconnected from the protrusion 14 in FIG. 2.

A free end 15 of the support arm 11 rotatably carries a pulley wheel 16 through which a dispense probe 17 extends.

A third pulley wheel 18 is also mounted to the support arm 11 and the position of its axis can be fixed (by means not shown) at a number of positions within an elongate slot 19.

A drive belt 20 extends around the drive pulley 8 and the pulley wheels 16,18, the position of the pulley wheel 18 being adjusted to tension the belt.

While the arm 11 is located in its first position as shown in FIGS. 1–3, rotation of the drive pulley 18 will cause rotation of the pulley wheel 16 and hence cause the dispense tube 17 to move around a circular path.

The pulley wheel 16 in the first position of the support arm 11 is located above a well unit support station 10 21 defined by a pair of juxtaposed slide guides 22 which receive in use a well unit support 23 from a well unit support transport system (not shown). This could have the form of the system shown in our co-pending European Patent Application No. 98307706.6. In this case, the well unit support 23 holds nine wells 24, one of which is indicated in FIG. 2. However, the invention is applicable to larger or smaller arrays of wells.

Laterally offset from the station 21 is a wash station 25 having an inlet tube 26 through which wash fluid is supplied and a drain outlet tube 27.

In operation, a liquid reagent supply tube (not shown) is connected to the dispense tube 17 and is connected via a computer controlled valve to a liquid reagent supply. The arm 11 is located in the position shown in FIGS. 1–3 and the dispense tube 17 will be positioned above the location of the first well 24. This is labelled 1 in FIG. 7. The wells 24 are then supplied to the station 21 and the motor 7 is activated. This causes clockwise rotation of the drive pulley 18 as viewed in FIG. 1, and this in turn causes clockwise rotation of the pulley wheel 16 and hence circular motion of the dispense tube 17. The motion of the tube 17 can be seen in FIG. 7 where it will be seen that it moves in turn between the wells labelled 18 respectively. As it is aligned with each well, the motor 7 is stopped and the liquid reagent valve opened to allow the correct quantity of reagent to be dispensed. The valve is then closed and the stepper motor actuated and the dispense tube 17 moved to the next well.

Figure 7:
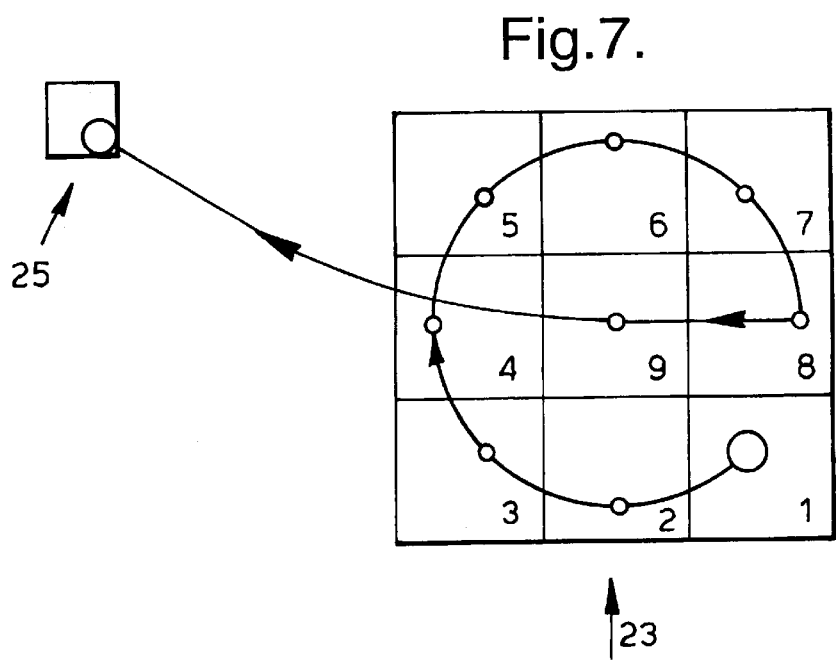

Once the dispense tube 17 has reached the well labelled 8 in FIG. 7, a pin 30 on the drive pulley 8 will engage a surface 31 of the arm 11. Further rotation of the drive pulley 8 will then cause rotation of the arm 11 about its axis 12.

This will cause the dispensing tube 17 to move to the well labelled 9 in FIG. 7 (first "second" position) and thereafter to the wash station 25 (second "second" position).

Figure 5:
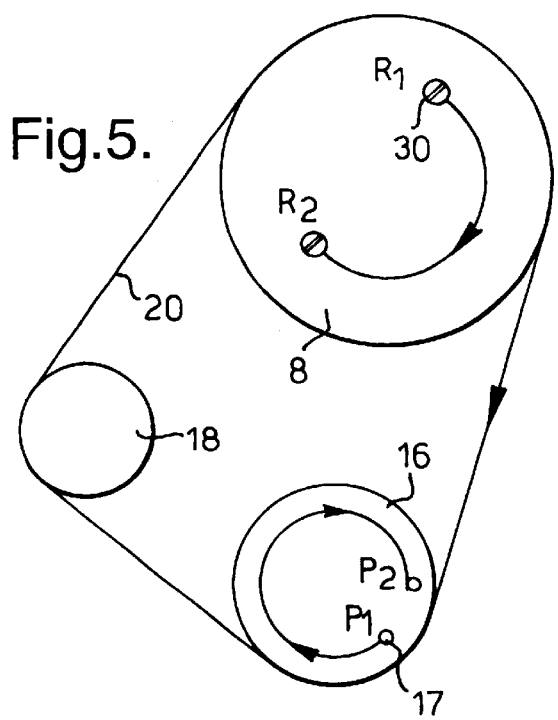
FIG. 5 illustrates the motion of the dispense probe when the support arm is in the first position.
Figure 6:
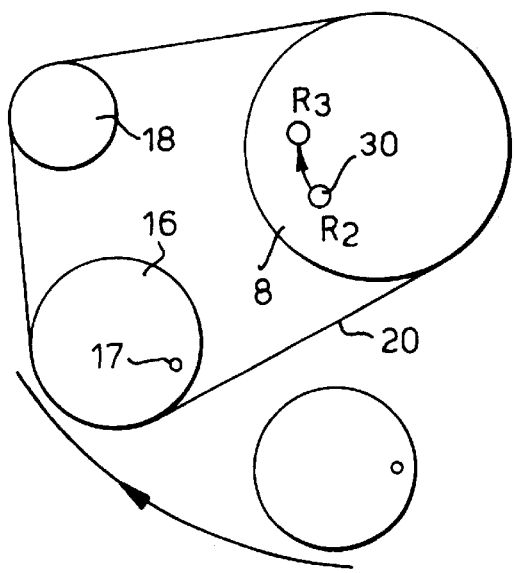
FIG. 6 illustrates motion of the support arm between the first and second positions; and, FIG. 7 illustrates schematically the path of the dispense probe.

This motion can be seen more clearly in FIGS. 5 and 6. In FIG. 5, it can be seen that rotation of the drive pulley 8 causes the pulley wheel 16 to move the dispense tube 17 from the position $P_1$ to $P_2$ while the pin 30 moves from position $R_1$ to $R_2$. Further rotation of the drive pulley 8, as seen in FIG. 6, causes the pin 30 to move from position $R_2$ to position $R_3$ and pivoting movement of the arm 11.

Once the dispense tube 17 is at the wash station 25 it will be washed in a conventional manner by introducing wash fluid through the inlet tube 26 so that it washes the end of the dispense tube 17 in the vicinity, the surplus wash fluid then draining out through the drain tube 27.

The motor 7 is then reversed so that the pin 30 returns to the position shown in FIG. 1 and the support arm 11 returns to its first position, under the influence of the spring 13, where it engages a stop (not shown). The spring 13 maintains contact between the surface 31 and the pin 30 until the arm 11 reaches its first position.

It will be understood that simple optical or other sensors may be attached, for example to the drive pulley 8 for position referencing purposes to the overall control system.

In the example described above, the arm 11 was movable o two "second" positions namely a further dispense position and a wash station. It is envisaged that one or more of the second positions could also be in the form of a pick-up position in which a liquid such as a diluent or buffer is aspirated for transfer to one of the other dispense positions. This would require the use of an aspirator tube which is mounted on the pulley wheel 16 and can be moved vertically.

We claim:

1. Liquid dispensing apparatus comprising a support member which supports a movably mounted dispensing member, the support member being movable between a first position and at least one second position; and a single drive system for causing the dispensing member to move relative to the support member to a number of dispense positions while the support member is in its first position and for causing the support member to move to the or each second position.

2. Apparatus according to claim 1, wherein the dispensing member is rotatably mounted to the support member.

3. Apparatus according to claim 2, wherein the dispensing member comprises a carrier rotatably mounted to the support member, and a dispensing tube mounted to the carrier.

4. Apparatus according to claim 1, wherein the drive system causes the dispensing member sequentially to move relative to the support member to the number of dispense positions while the support member is in its first position and thereafter causes the support member to move to the or each second position.

5. Apparatus according to claim 1, wherein the support member is pivoted to a base for rotational movement between the first and second positions.

6. Apparatus according to claim 5, wherein the drive system includes a rotationally mounted drive member which rotates upon actuation of the drive system from first to second positions, during which the dispensing member moves to each of the dispense positions, and thereafter to one or more third positions while engaging the support member so as to rotate the support member to corresponding second positions.

7. Apparatus according to claim 6, wherein the rotatably mounted drive member is a pin supported on a rotatably mounted drive pinion.

8. Apparatus according to claim 1, wherein the support member is urged towards the first position.

9. Apparatus according to claim 1, wherein the drive system includes a drive belt linking a drive motor of the drive system and the dispensing member.

10. Apparatus according to claim 1, wherein the or one of the second positions comprises a wash station.

11. Apparatus according to claim 1, wherein the or one of the second positions comprises a further dispense position.

* * * * *